United States Patent [19]

Saito et al.

[11] Patent Number: 5,318,905
[45] Date of Patent: Jun. 7, 1994

[54] COMPOSITION CONTAINING CELLULASE FROM BACILLUS FERM BP-3431 OR A MUTANT STRAIN THEREOF AND PAPER PULP AND METHOD OF USING CELLULASE TO TREAT PAPER PULP SLURRY

[75] Inventors: Kiyoshi Saito; Masahiko Seko; Eiko Masatsuji, all of Tokyo, Japan

[73] Assignee: Showa Denko K.K., Tokyo, Japan

[21] Appl. No.: 59,169

[22] Filed: Mar. 11, 1993

Related U.S. Application Data

[62] Division of Ser. No. 734,662, Jul. 23, 1991, Pat. No. 5,231,022.

[30] Foreign Application Priority Data

Jul. 24, 1990 [JP] Japan .................................. 2-193883

[51] Int. Cl.⁵ .......................... C12N 9/42; C12N 1/22; C12N 1/00; D21F 11/00
[52] U.S. Cl. .................................. 435/209; 435/832; 435/252.31; 162/158
[58] Field of Search .................. 435/209, 832, 252.31; 162/158

[56] References Cited

U.S. PATENT DOCUMENTS

| | | | |
|---|---|---|---|
| 3,844,890 | 10/1974 | Horikoshi et al. | 435/209 |
| 3,983,002 | 9/1976 | Ohya et al. | 435/209 |
| 4,945,053 | 7/1990 | Ito et al. | 435/209 |
| 4,962,030 | 10/1990 | Kawai et al. | 435/209 |
| 5,045,464 | 9/1991 | Ito et al. | 435/209 |

FOREIGN PATENT DOCUMENTS

| | | |
|---|---|---|
| 269977 | 6/1988 | European Pat. Off. . |
| 383999 | 9/1989 | European Pat. Off. . |
| 0339550 | 11/1989 | European Pat. Off. . |
| 395792 | 11/1990 | European Pat. Off. . |
| 58-224686 | 12/1983 | Japan . |
| 59-009299 | 1/1984 | Japan . |
| 60-226600 | 11/1985 | Japan . |
| 61-19483 | 1/1986 | Japan . |
| 61-280282 | 10/1986 | Japan . |
| 62-296874 | 12/1987 | Japan . |
| 63146786 | 6/1988 | Japan . |
| 1269495 | 10/1989 | Japan . |
| 280683 | 3/1990 | Japan . |
| 2435 | 5/1990 | Japan . |
| 2215381 | 8/1990 | Japan . |
| 1465307 | 2/1977 | United Kingdom . |
| 2094826 | 9/1982 | United Kingdom . |
| 2095275 | 9/1982 | United Kingdom . |

OTHER PUBLICATIONS

Tappi Journal 73 (12) 197–202, 1990, Pommier et al., "Using Enzymes to Improve the Process and the Product Quality in the Recycled Paper Industry", Part 2: Industrial Applications.

Tappi Journal 72 (6) 197–201, 1989, Pommier et al., "Using Enzymes to Improve the Process and the Product Quality in the Recycled Paper Industry", Part 1: The Basic Laboratory Work.

(List continued on next page.)

Primary Examiner—David M. Naff
Assistant Examiner—Michael V. Meller
Attorney, Agent, or Firm—Sughrue, Mion, Zinn, Macpeak & Seas

[57] ABSTRACT

A cellulase is provided having the following properties: (1) an optimum pH of from 9.5 to 10.5 as measured using carboxymethylcellulose as a substrate; (2) a stable pH of from 6 to 11 as measured using carboxymethylcellulose as a substrate after treating at 30° C. and for 30 minutes; (3) an optimum temperature of about 55° C. as measured using carboxymethylcellulose as a substrate; (4) influence of a surfactant being such that residual activity is 90% or more after treatment at 30° C. and pH of 9.0 for 2 hours in the presence of a sodium n-alkylbenzenesulfonate; (5) a molecular weight of $52,000 \pm 2,000$ as measured by electrophoresis on SDS-polyacrylamide gel; and (6) an isoelectric point of $4.2 \pm 0.2$ as measured by isoelectric electrophoresis. The cellulase is produced by Bacillus FERM BP-3431 or a mutant strain thereof. Also disclosed is a detergent comprising the cellulase, a builder and a surfactant. A composition and a method of treating a paper pulp slurry is also disclosed.

3 Claims, 3 Drawing Sheets

OTHER PUBLICATIONS

J. Bacteriology 124 (1) 48–54, 1975, Yoneda et al., "Mutation of Bacillus Subtilis Causing Hyperproduction of α-Amylase and Protease, and its Synergistic Effect".

Applied Environmental Microbiology 43 777–780, 1982, Teather et al., "Use of Congo Red-Polysaccharide Interactions in Enumeration and Characterization of Cellulolytic Bacteria from Bovine Rumen".

J. Gen. Microbiology 136 1327–1334, 1990, Ozaki et al., "Molecular Cloning and Nucleotide Sequence of a Gene for Alkaline Cellulase from Bacillus sp. KSM-635".

Appl. Microbiol. Biotechnol. 31 265–271, 1989, Huang et al., "Molecular Cloning and Expression of Multiple Cellulase Genes of Ruminococcus Flavefaciens Strain 186 in *Escherichia coli*".

J. Gen. Microbiology 131 3339–3345, 1985, Fukumori et al., "Purification and Properties of a Cellulase from Alkalophilic Bacillus sp. No. 1139".

Agric. Biol. Chem. 54 (1) 91–96, 1990, Shikata et al., "Alkaline Cellulases for Laundry Detergents: Production by Alkalophilic Strains of Bacillus and Some Properties of the Crude Enzymes".

COMPOSITION CONTAINING CELLULASE FROM BACILLUS FERM BP-3431 OR A MUTANT STRAIN THEREOF AND PAPER PULP AND METHOD OF USING CELLULASE TO TREAT PAPER PULP SLURRY

This is a divisional of application Ser. No. 07/734,662 filed Jul. 23, 1991, now U.S. Pat. No. 5,231,022.

BACKGROUND OF THE INVENTION

1. Field of the Invention

The present invention relates to a novel cellulase, and a method for producing the same as well as use thereof as an aid for detergents or as a paper treating agent.

2. Description of Prior Art

Development of cellulases has been carried out with view to efficient utilization of biomass resources, particularly cellulose resources. However, utilization of cellulases for biomass on an industrial scale has prevailed not so widely.

On the other hand, as a novel industrial application of cellulase, it has been known that cellulase is effective for increasing the washing power of detergents. For example, it has been confirmed that cellulase is effective for washing denim due to its ability of removing fine fiber dusts (cf. British Patent Nos. 2094826 and 2095275). There have been published many publications on the utilization of cellulase in various steps of paper making such as deinking of waste-paper, bleaching of pulp, and improvement of production processes for regenerated paper and much attention has been directed to cellulase (cf. Japanese Patent Publication Laid-Open Nos. 9299/1984, 80683/1990, European patent Publications Nos. 395792 and 383999, and Tappi Journal vol. 72, No. 6, 197-201 (1989) and vol. 73, No. 12, 197-202 (1990)).

However, under ordinary washing conditions pH of washing liquor is on a higher alkalinity side, and a part of paper making steps is carried out under highly alkaline conditions, resulting in that cellulases used in washing or paper making processes must be alkaline cellulases which can function under highly alkaline conditions. Furthermore, the cellulases must be those which can function stably in the presence of detergents or anionic surfactants used in a part of paper making steps.

Alkaline cellulases produced by microorganisms include those produced by a method in which an alkalophilic bacterium belonging to the genus Bacillus is cultivated and an alkaline cellulase produced is collected (cf. U.S. Pat. No. 3,844,890), a method in which an alkalophilic bacterium belonging to the genus Cellulomonas is cultivated to produce alkaline cellulase 301-A (cf. Japanese Patent Publication Laid-Open No. 224686/1983), and a method in which an alkalophilic bacterium belonging to the genus Bacillus KSM-635 is cultivated to produce alkaline cellulase K (cf. U.S. Pat. No. 4,945,053), respectively. However, these known cellulases are not always stable enough against an anionic surfactant which is one component of detergent. Therefore, there has been a keen demand for development of cellulases which are more stable than ever against anionic surfactants.

SUMMARY OF THE INVENTION

An object of the present invention is to provide a novel cellulase which has an optimum pH in a higher alkalinity region and is stable against anionic surfactants.

Another object of the present invention is to provide a method for producing such a cellulase.

Still another object of the present invention is to provide an aid for detergents containing such a cellulase as an effective ingredient.

Yet another object of the present invention is to provide a paper treating agent containing such a cellulase as an effective ingredient.

In order to obtain a cellulase having the aforementioned properties, the present inventors have searched a number of microorganisms by isolating and cultivating them, and as a result the present inventors have found that a bacterium belonging to the genus Bacillus isolated from the soil collected in the suburbs of Tokyo, i.e., Bacillus sp. SD402, can produce a novel cellulase which has excellent properties in an alkalin condition, thus is suitable as an aid for detergents and as a paper treating agent. The present invention is based on this discovery.

That is, according to a first aspect of the present invention, there is provided a cellulase having the following properties: (1) an optimum pH of from 9.5 to 10.5 as measured using carboxymethylcellulose as a substrate; (2) a stable pH of from 6 to 11 as measured using carboxymethylcellulose as a substrate; (3) an optimum temperature of about 55° C. as measured using carboxymethylcellulose as a substrate; (4) influence of a surfactant being such that residual activity is 90% or more after treatment at 30° C. and pH of 9.0 for 2 hours in the presence of a sodium n-alkylbenzene-sulfonate; (5) a molecular weight of $52,000 \pm 2,000$ as measured by electrophoresis; and (6) an isoelectric point of $4.2 \pm 0.2$ as measured by isoelectric electrophoresis.

According to a second aspect of the present invention, there is provided a method for producing a cellulase comprising the steps of: cultivating in a medium a microorganism belonging to the genus Bacillus and having an ability of producing the above-described cellulase; and collecting the objective cellulase from the medium. Here, the microorganism may be Bacillus sp. SD402 strain, its mutant strains or its genetic engineered strains.

According to a third aspect of the present invention, there is provided an aid for detergents which comprises the above-described cellulase as an effective ingredient.

According to a fourth aspect of the present invention, there is provided a paper treating agent comprising the above-described cellulase as an effective ingredient.

DETAILED DESCRIPTION OF THE INVENTION

Figure 1:
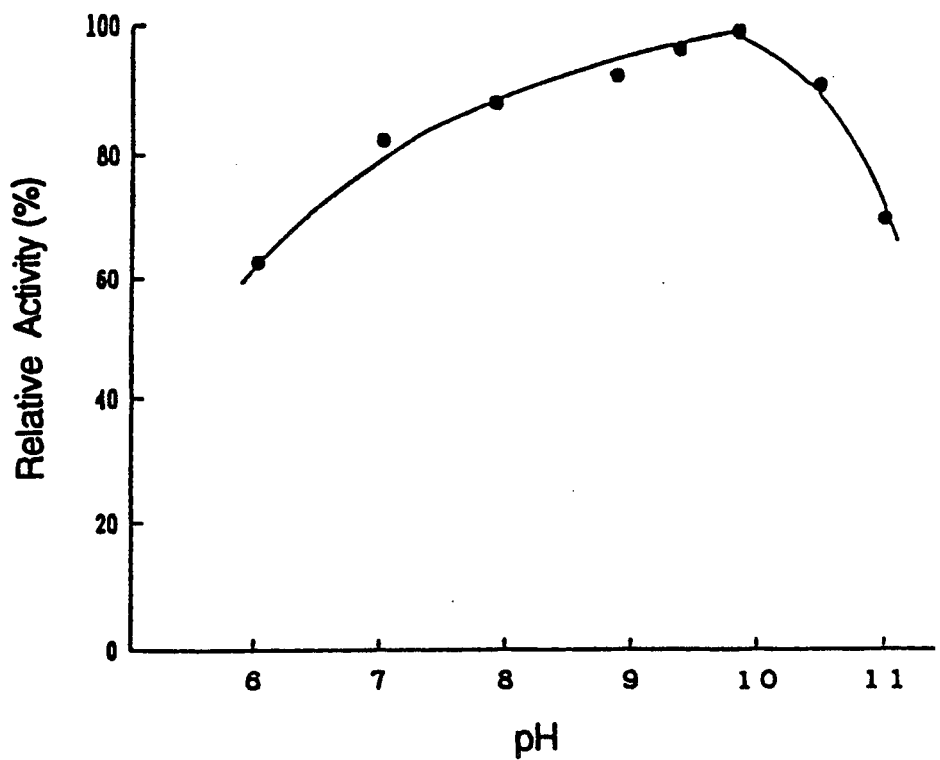
FIG. 1 illustrates the relative activity of the cellulase of the present invention at different pH conditions.

Hereafter, detailed explanation will be made on the novel strain producing the cellulase of the present invention, the cellulase, method for producing it and its utility.

Cellulase-Producing Microorganism

The microorganism used for producing the novel cellulase of the present invention is a bacterium belonging to the genus Bacillus and having an ability of producing cellulase having the aforementioned properties. The bacterium has the following properties.

(a) Morphology
| | | |
|---|---|---|
| (1) | Form and size of cell: | Rod with a size of 0.3 to 0.5 × 2.8 to 5.2 μm. |
| (2) | Polymorphism of cell: | None. |
| (3) | Motility: | *Peritrichous flagella.* |
| (4) | Spore formation: | Forms elliptical spores with a size of 1.0 to 1.5 × 1.8 to 2.2 μm. |
| (5) | Gram stain: | Positive. |
| (6) | Acid-fast stain: | Negative. |

(b) Growth on the following media
| | | |
|---|---|---|
| (1) | Meat broth agar plate medium: | Circular colonies with flat surfaces and slight protrusions in central portions thereof. Yellowish white and translucent. |
| (2) | Meat broth agar slant medium: | Cloth spreading form. |
| (3) | Meat broth liquid medium: | Turbid. |
| (4) | Meat broth gelatin stab culture medium: | Liquefaction. |
| (5) | Litmus milk: | Neither coagulated nor peptonized. |

(c) Physiological Properties
| | | |
|---|---|---|
| (1) | Reduction of nitrates: | Negative. |
| (2) | Denitrification reaction: | Negative. |
| (3) | MR test: | Negative. |
| (4) | VP test: | Negative. |
| (5) | Production of indole: | Negative. |
| (6) | Production of hydrogen sulfide: | Negative. |
| (7) | Hydrolysis of starch: | Positive. |
| (8) | Assimilation of citric acid: | Negative. |
| (9) | Assimilation of inorganic nitrogen: | Assimilate nitrates and ammonium salts. |
| (10) | Production of Pigments: | Negative. |
| (11) | Urease: | Negative. |
| (12) | Oxidase: | Positive. |
| (13) | Catalase: | Positive. |
| (14) | Growth range (pH): | Grows at 8.0 but does not grow at 7.1. Grows at 10.8 but does not grow at 12.3. |
| | (temperature): | Grows at 15° C. and 40° C. but does not grow at 50° C. |
| (15) | Behavior to oxygen: | Aerobic. |
| (16) | O-F test: | Fermentative. |
| (17) | Production of acid from sugars and gas formation: | |

| Sugar | Acid | Gas |
|---|---|---|
| 1) L-Arabinose | + | − |
| 2) D-Xylose | + | − |
| 3) D-Glucose | + | − |
| 4) D-Mannose | + | − |
| 5) D-Fructose | + | − |
| 6) D-Galactose | + | − |
| 7) Maltose | + | − |
| 8) Sucrose | + | − |
| 9) Lactose | + | − |
| 10) Trehalose | + | − |
| 11) D-Sorbitol | − | − |
| 12) D-Mannitol | − | − |
| 13) Inositol | − | − |
| 14) Glycerol | − | − |
| 15) Starch | + | − |

On the aforementioned bacteriological characteristics, "Bergey's Manual of Systematic Bacteriology (1986)" and "Agriculture Handbook, No. 427, The Genus Bacillus (U.S. Dept. of Agr. 1973)" were consulted and the instant bacterial strain was identified as a sporangium bacillus and more specifically as a strain similar to *Bacillus alcalophilus* in view of its motility, gram stain, aerophilicity, growth pH range and other properties. Accordingly, the instant strain was called Bacillus sp. SD402.

Comparing the characteristics of Bacillus sp. SD402 with those of *Bacillus alcalophilus* described in "Bergey's Manual of Systematic Bacteriology", among others with "production of acid from sugar", the following differences are noted:

| Kind of Sugar | Bacillus sp. SD402 | *Bacillus alcalophilus* |
|---|---|---|
| D-Sorbitol | − | + |
| D-Mannitol | − | + |
| Glycerol | − | + |

When cultivating a standard strain NCIB10438 of *Bacillus alcalophilus* described in the Bergey's Manual and the instant strain under the same culture conditions and comparing bacteriological characteristics between the two strains, the following differences are noted:

| | Bacillus sp. SD402 | NCIB10438 |
|---|---|---|
| Growth on meat broth agar plate medium | Yellowish white translucent | Yellow opaque |
| Litmus milk | Neither coagulation nor peptonization | Peptonization |
| Production of acid from sugar | | |
| L-Arabinose | + | − |
| D-Galactose | + | − |
| Lactose | + | − |

From the above results, the strain of the present invention has been identified to be a novel strain which is taxonomically similar to *Bacillus alcalophilus* but has different characteristics from the known strains.

Bacillus sp. SD402 strain of the present invention has been deposited at Fermentation Research Institute, Agency of Industrial Science and Technology, Ministry of International Trade and Industry 1-3, Higashi 1-chome, Tsukuba-shi, Ibaraki-ken, 305, Japan, under "Budapest Treaty on the International Recognition of the Deposit of Microorganisms for the Purpose of Patent Procedure" under Accession No. Ferm BP-3431 on Jun. 14, 1990.

The microorganism used in the production of the cellulase of the present invention is not limited to the aforementioned Bacillus sp. SD402 strain but any strain may be used so far as it can produce a cellulase having the characteristics as explained hereinbelow. Bacillus sp. SD402 may also include its natural or artificial mutants and genetically engineered variations.

Artificial mutants of Bacillus sp. SD402 can be obtained by a conventional method. For example, an original strain is subjected to artificial mutation treatment such as irradiation with ultraviolet rays or treatment with a chemical, e.g., N-methyl-N'-nitro-N-nitrosoguanidine (NTG), and then planted on an agar medium containing L-broth (yeast extract, peptone, NaCl, and glucose) adjusted to pH about 9 with sodium carbonate and about 0.1 to 0.2% by weight of carboxymethylcellulose (CMC) and cultivated for 1 or 2 days to allow colonies to grow. Each colonies are divided into two groups. One is transplanted on agar plate containing L-broth and another on agar plate containing CMC-added L-broth adjusted at pH 9.0 respectively. The colony group on CMC-added L-broth was dipped in an aqueous solution of Congo Red and left to stand for a while, and then washed with saline. Among colonies having decolored, relatively transparent haloes is selected one having the largest halo, and corresponding strain which grows on agar plate containing L-broth (not added CMC) is obtained. This strain is then cultivated on a conventional medium for cellulase production, and the resulting cellulase is checked for identity. Thus, a strain having the most excellent productivity for the objective cellulase can be screened (cf. Applied Environmental Microbiology, Vol. 43, 777–780 (1982)).

Genetic engineered strain can be obtained also by a conventional method. For example, entire chromosomal DNA is extracted from the original strain and digested with a suitable restriction enzyme to obtain DNA fragment.

The chromosomal DNA fragment thus obtained is incorporated in a suitable vector and introduced in a cellulase non-producing strain and cellulase production is checked. The DNA fragment of which cellulase production has been confirmed is introduced in the original strain or a strain having a higher enzyme productivity (i.e., having a higher ability of secreting proteins) using a suitable vector such as a plasmid to obtain a strain of which productivity has been improved (cf. General Microbiology, 136, 1327–1334, 1990 and Appl. Microbiology Biotechnology 31, 256–271, 1989).

Cultivation Method

Upon production of the cellulase of the present invention, there is no special requirement on the method for cultivating the aforementioned microorganism and it can be cultivated by a conventional method appropriately.

As the nutrient sources of the medium, those usually used for cultivation of microorganisms may be used. Carbon source may be any assimilable carbon compounds or those containing them, for example, glucose, maltose, starch, CMC, etc. Nitrogen source may be assimilable nitrogen compounds or those containing them, for example, ammonium salts, peptone, soybean powder, defatted soybean powder, etc. Inorganic salts include salts such as phosphates, and magnesium salts. In addition, various organic or inorganic substances necessary for growth of bacterium and production of enzymes or materials containing them, for example, vitamins, yeast extract, etc. may be added to the culture medium.

Cultivation may be carried out either in a liquid medium or on a solid medium. Liquid culture is preferred. Conditions for liquid culture should be optimized for the production of the objective cellulase although such conditions may vary more or less depending on the composition of the medium used. The cultivation temperature is within the range of 25° to 35° C., and cultivation time is within the range of about 12 hours to about 3 days, and the cultivation may be stopped when cellulase production has reached the maximum. pH of the medium is usually 8 or higher, and pH 9 to 10 is preferable for the cellulase production. By conducting cultivation as described above, the objective cellulase can be obtained in the liquid culture medium.

Isolation and Purification Methods

The cellulase of the present invention can be isolated from the liquid culture medium obtained as described above and purified by conventional methods for collecting the enzyme. That is, cells and solids derived from the medium can be removed by a suitable conventional separation method such as filtration or centrifugation to obtain supernatant or filtrate. After concentrating it, the liquid thus separated can be spray-dried, or lyophilized, or alternatively the separated liquid without being concentrated can be salted out with addition of a soluble salt or precipitated with addition of a hydrophilic organic solvent, to obtain a cellulase. The enzyme can be further purified by one or more purification means such as adsorptional elimination with an ion exchange resin, and gel filtration.

Properties of Enzyme

Properties of the cellulase of the present invention will be described in detail below.

Assay of Enzyme Activities (1) Carboxymethylcellulase (CMCase) Activity

Assay is carried out using as a substrate a solution of carboxymethylcellulose (CMC) in M/20 sodium carbonate-M/20 boric acid-potassium chloride buffer (pH 9.0). More specifically, 0.1 ml of the enzyme is added to 0.9 ml of a substrate solution obtained by dissolving CMC in M/20 sodium carbonate-M/20 boric acid-potassium chloride buffer (pH 9.0) so as to form a 0.5% by weight solution (pH 9.0), and reaction is carried out at 30° C. for 15 minutes. After completion of the reaction, determination of reducing sugars is carried out by p-hydroxybenzoic acid hydrazide method (PHBAH method). That is, 3.0 ml of PHBAH reagent is added to 1.0 ml of the reaction mixture, and the resulting mixture is heated at 100° C. for 10 minutes for color development. After cooling, optical density is measured at 410 nm. Assay of the enzyme is expressed in terms of unit (U) which is unity (1 U) when a reducing sugar equivalent to 1 $\mu$mol of glucose is produced for 1 minute.

(2) Avicelase Activity

After Avicel (Merck) was pretreated to remove water-soluble fraction and suspended in M/20 sodium carbonate-M/20 boric acid-potassium chloride buffer solution (pH 9.0). More specifically, 0.1 ml of the cellulase solution was added to 0.9 ml of 1.0 % Avicel (pH 9.0) and the mixture was reacted at 30° C. for 30 minutes. After completion of the reaction, 3.0 ml of PHBAH reagent was added to 1.0 ml of the reaction mixture. The resulting mixture was heated at 100° C. for 10 minutes for color development. After being cooled, the reaction mixture was measured colorimetrically at a wavelength of 410 nm. Assay of the cellulase was defined to be unity (1 U) when the cellulase produced a reducing sugar equivalent to 1 $\mu$mol of glucose in 1 minute under the aforementioned conditions.

(3) β-Glucosidase Activity and p-nitrophenylcellobioside decomposition Activity Activity of the cellulase of the present invention as β-glucosidase is determined using p-nitrophenyl β-D-glucopyranoside (pNPG) and also activity for decomposing p-nitrophenylcellobioside is determined using p-nitropehnyl β-D-cellobioside (pNPC). Both pNPG and pNPC are synthetic substrates. More specifically, 0.1 ml of cellulase solution is added to a substrate solution composed of 1.5 ml of M/20 sodium carbonate-M/20 boric acid-potassium chloride buffer (pH 9.0) and 0.1 ml of 50 mM pNPG or 5 mM pNPC, and the resulting mixture is reacted at 30° C. for 30 minutes. p-Nitrophenol released is determined by colorimetry at 400 nm. The amount of the cellulase which can release 1 μmol of p-nitrophenol for 1 minute under the same conditions is defined as unity (1 U).

Properties of Enzyme

(1) Action

The cellulase of the present invention acts to hydrolyze μ-glucoside bonds on carboxymethylcellulose (CMC) and highly crystallized cellulose such as Avicel. It also acts to release p-nitrophenol on p-nitrophenylcellobioside, one of synthetic substrates.

(2) Substrate Specificity

The cellulase of the present invention acts on CMC, Avicel, p-nitrophenyl β-D-cellobioside (pNPC) but does not act on p-nitrophenyl β-D-glucopyranoside (pNPG). Assuming the CMCase activity is 100, the cellulase exhibits a relative Avicelase activity of 0.04 and a relative pNPC decomposition activity of 0.3.

| Substrate | Relative Activity |
|---|---|
| CMC | 100 |
| Avicel | 0.04 |
| pNPG | 0 |
| pNPC | 0.3 |

(3) Optimum pH

The cellulase is reacted with CMC as a substrate at 30° C. for 15 minutes at different pH conditions using Britton-Robinson buffer solutions and the activity is measured. FIG. 1 illustrates the relationship between the pH at which reaction proceeds and the relative activity. Thus the optimum pH is measured as 9.5 to 10.5.

(4) Stable pH Range

Figure 2:
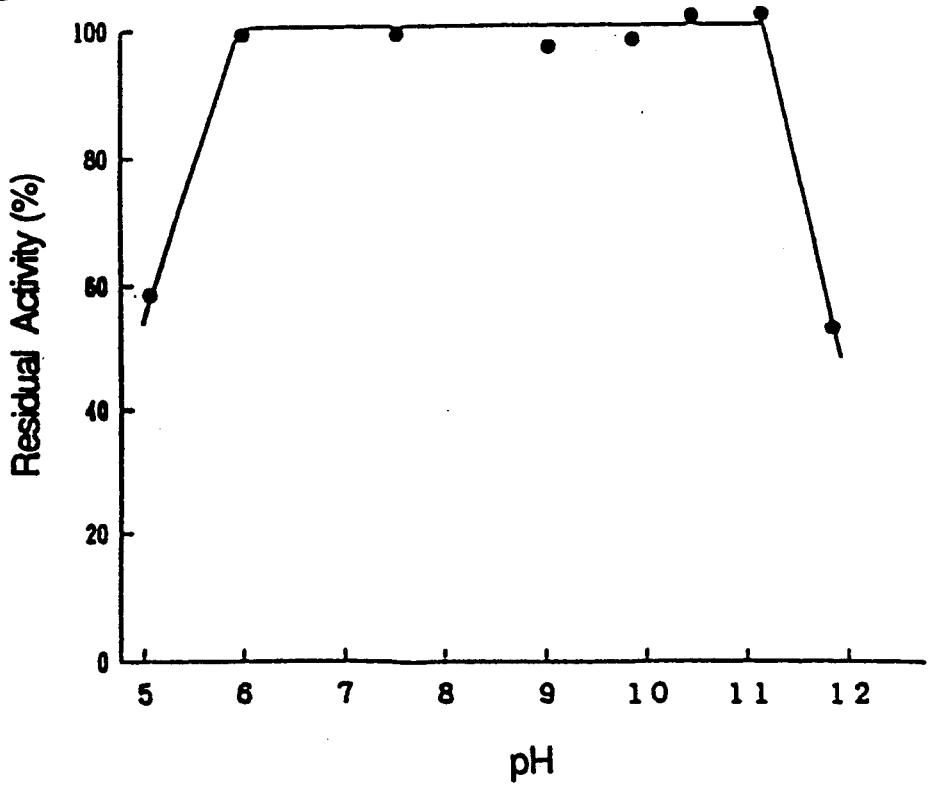
FIG. 2 illustrates the residual activity of the cellulase of the present invention at different pH conditions.

The cellulase is left in various Britton-Robinson buffer solutions with different pH at 30° C. for 30 minutes, and then its activity is measured after the reaction at 30° C. for 15 minutes using CMC as a substrate. FIG. 2 illustrates the relationship between the pH at which treatment is carried out and the residual activity of the cellulase. Thus stable pH is measured to be 6 to 11.

(5) Optimum Temperature

Figure 3:
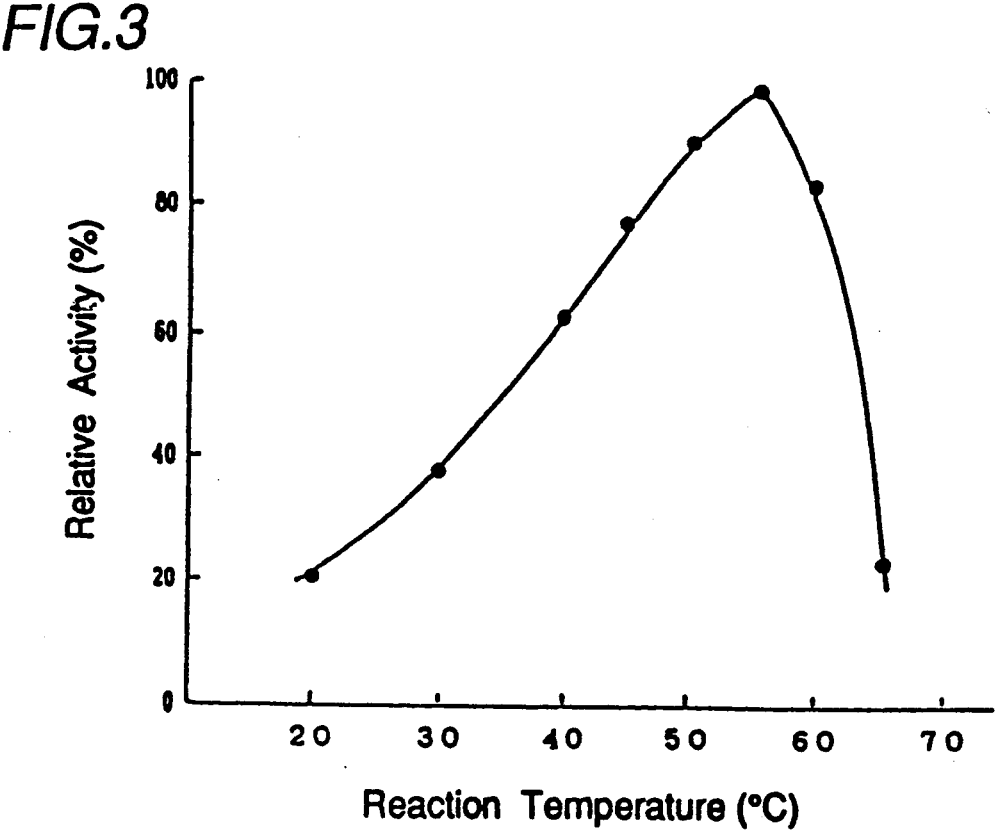
FIG. 3 illustrates the relative activity of the cellulase of the present invention at different reaction temperature.

The cellulase is reacted with CMC at pH 9.0 for 15 minutes at different temperatures. FIG. 3 illustrates the relationship between the reaction temperature and the relative activity of the cellulase. Thus the optimum temperature of the cellulase is measured as about 55° C.

Figure 4:
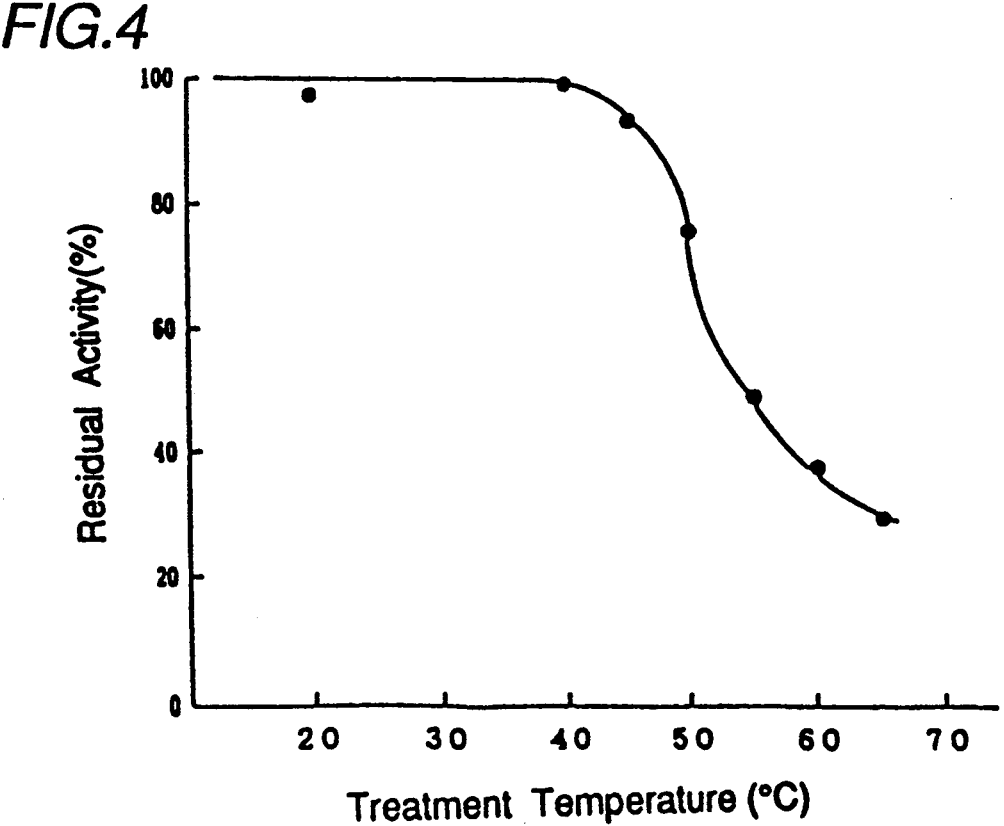
FIG. 4 illustrates the residual activity of the cellulase of the present invention at different temperature.

(6) Thermal Stability when it is heated at various temperatures (5° to 65° C.) for 30 minutes in M/20 sodium carbonate-M/20 boric acid-potassium chloride buffer (pH 9.0), the cellulase shows no deactivation up to near 40° C., having about 50% residual activity at 55° C. and about 30 % residual activity at 65° C. FIG. 4 illustrates the relationship between the treatment temperature and the residual activity of the cellulase.

(7) Influences of Enzyme Inhibitors, Metal Ions and Chelating Agents

The cellulase of the present invention is inhibited with $Cu^{++}$ (5 mM), or p-mercurybenzoic acid (5 mM) but is activated with $Ca^{++}$ (5 mM). EDTA (5 mM) has no influence on the activity of the cellulase.

(8) Influence of Surfactant

Figure 5:
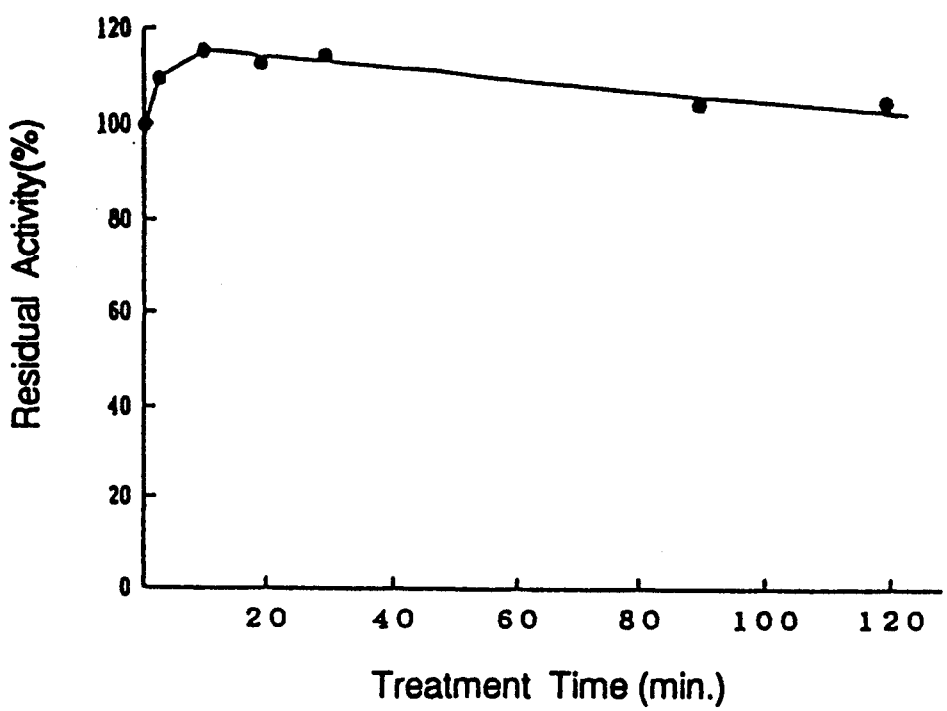
FIG. 5 illustrates the residual activity of the cellulase of the present invention when treated in the presence of 3,000 ppm of a sodium n-alkylbenzenesulfonate at 30° C. and pH of 9.0.

Almost no deactivation is observed when treated at 30° C. and pH of 9.0 for 2 hours in the presence of a sodium n-alkylbenzenesulfonate in a concentration of 3,000 ppm. FIG. 5 illustrates the relationship between the treatment time and the residual activity of the enzyme.

(9) Molecular Weight

Molecular weight of the cellulase of the present invention measured by SDS-polyacrylamide gel electrophoresis method is 52,000±2,000.

(10) Isoelectric Point

Isoelectric point of the cellulase of the present invention measured by polyacrylamide gel electrophoresis method is 4.2±0.2.

The cellulase of the invention is produced by a novel strain belonging to the genus Bacillus, i.e., Bacillus sp. SD402, and has an optimum pH in a higher alkalinity pH region.

Comparing the cellulase of the invention with alkaline cellulases produced by known Bacillus strains, the following differences are noted, which indicate that the cellulase of the present invention is clearly different from the known ones and it is evident that the cellulase of the invention is a novel alkaline cellulase.

| | Optimum pH | Optimum Temperature | Molecular Weight |
|---|---|---|---|
| Cellulase of the present invention | 9.5–10.5 | 55° C. | 52,000 ± 2,000 |
| U.S. Pat. No. 3,844,890 | 8–9 | 50° C. | 30,000 |
| U.S. Pat. No. 4,945,053 | | | |
| Alk. cellulase K | 9–10 | 40° C. | 180,000 ± 10,000 |
| CMCase I | 9.5 | 40° C. | 145,000 ± 10,000 |
| CMCase II EP269977 | 9.5 | 30–40° C. | 170,000 ± 20,000 |
| Alk. cellulase K-425 | 8–10 | 50° C. | 35,000 |
| Alk. cellulase K-521 | 7–10 | 60° C. | 31,000 |
| Alk. cellulase K-580 | 7–10 | 65° C. | 18,000 or 50,000 |
| Alk. cellulase K-522 | 7–10 | 60° C. | 35,000 |
| Alk. cellulase E-II | 7–10 | 50° C. | 34,000 or 61,000 |
| Alk. cellulase E-III | 7–9 | 50° C. | 35,000 or 61,000 |
| J. Gen. Microbiology 131 3339–3345, 1985 | 9 | No Data | 92,000 |
| Agric. Biol. Chem. | 8.5–9.5 | 50° C. | No Data |

| | Optimum pH | Optimum Temperature | Molecular Weight |
|---|---|---|---|
| 54(1) 91-96, 1990 | | | |

The cellulase of the present invention has a high optimum pH as high as 9.5 to 10.5, and even at pH 11 still retains a relative activity of about 70% of the activity at the optimum pH, and at pH 6 a relative activity of about 60% of the activity at the optimum pH, thus retaining activity within a broad pH range. Further, it retains activity at low temperatures.

The utility of the cellulase of the present invention is not limited particularly and the cellulase can be used in various fields making the most of the aforementioned characteristics. Typical examples of the utility of the cellulase include an aid for laundry detergents and a paper treating agent to improve washing power or paper making processes because it has a high stability against anionic surfactants used in laundry detergents or employed in paper making processes.

The amount of the cellulase used is not strictly prescribed because it may vary depending on purposes, formulations, activities and the like. For example, a formulation as an aid for laundry detergents contains about 0.1 to 10% by weight of the cellulase assuming that its activity is 100 u/g of said cellulose based on the weight of the detergent components including a builder, a surfactant, etc. In a formulation as a paper treating agent, about 0.1 to 2% by weight of the cellulase is added to a slurry containing 3 to 10% by weight of pulp. Use of the cellulase having a higher activity results in reduction in the amount of the cellulase to be added.

EXAMPLES

Hereafter, the present invention will be explained in more detail by way of examples. However, the present invention is not limited thereto. Unless otherwise indicated specifically, all percentages and parts are by weight.

EXAMPLE 1

Aliquots of a liquid culture medium composed of 1% peptone, 0.5% sodium chloride, 0.1% dipotassium hydrogenphosphate, 0.05% magnesium sulfate, 0.5% yeast extract, 0.5% cellobiose, 0.5% CMC, and 0.5% sodium carbonate were introduced in test tubes respectively and the test tubes were sterilized by a conventional manner. SD402 strain was inoculated in the test tubes, which were then incubated with shaking at 35° C. for 25 hours. The culture medium was centrifuged, and supernatant was measured for its cellulase activity. Activity was 0.2 U/ml.

EXAMPLE 2

A liquid culture medium composed of 2% soybean powder, 0.5% sodium chloride, 0.1% dipotassium hydrogenphosphate, 0.02% magnesium sulfate, 0.5% yeast extract, 0.5% maltose, 0.1% CMC, and 0.3% sodium carbonate was charged in a 5 liter-fermenter and steam-sterilized. To this medium was inoculated Bacillus sp. SD402 strain previously cultivated, and incubated at 35° C. for 35 hours with aeration and stirring. The culture broth was centrifuged to obtain supernatant. The supernatant had a cellulase activity of 1.1 U/ml. The supernatant (1.3 liters) was concentrated using an ultrafiltration membrane, lyophilized to obtain a crude enzyme having a specific cellulase activity of 100 U/g.

EXAMPLE 3

The cellulase of the present invention was purified from the crude enzyme obtained in Example 2.

Figure 6:
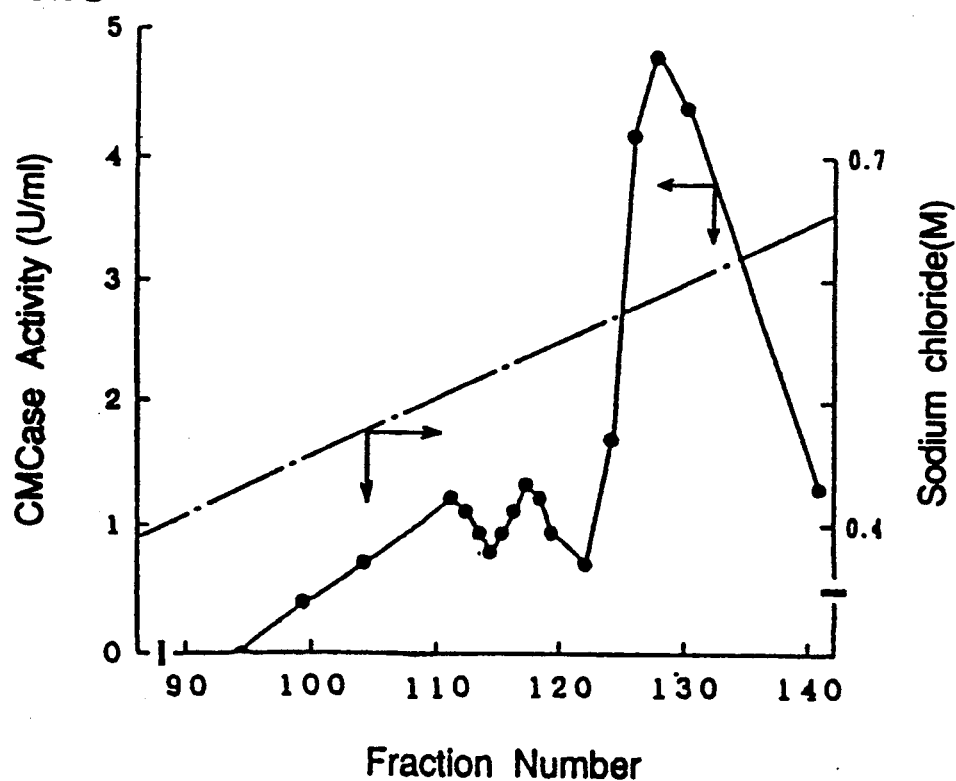
FIG. 6 illustrates the CMCase activities of each fractions with diethylaminoethyl (DEAE) anion exchange resin of a crude enzyme obtained from SD402 strain of the invention.

The crude enzyme (4 g) was dissolved in 200 ml of 10 mM sodium carbonate-10 mM boric acid-potassium chloride buffer solution (pH 9), and precipitate corresponding to 20 to 70% fraction was obtained by a conventional ammonium sulfate precipitation method. The precipitate was dissolved in the aforementioned buffer solution. After being desalted with an ultrafiltration membrane, the solution was purified with CM (carboxymethyl)-cation exchange resin column (diameter: 25 mm, length: 30 cm) equilibrated with 10 mM bis-Tris buffer solution (pH 7.0). The active fractions eluted by this operation were concentrated and desalted with an ultrafiltration membrane, and then adsorbed on DEAE (diethylaminoethyl) anion exchange resin column (diameter: 25 mm, length: 36 cm), followed by elution with sodium chloride at a density gradient (0 to 1M). As a result, the crude enzyme contained at least three types of cellulase having different CMCase activities. FIG. 6 illustrates CMCase activities of each fractionations with DEAE anion exchange resin. Fraction of fraction numbers from 122 to 141, main component having most excellent CMCase activity among others, was concentrated and desalted with an ultrafiltration membrane, and then purified with the same DEAE anion exchange resin. The active fractions which eluted by this operation were desalted with an unltrafiltration membrane, lyophilized, dissolved in 10 mM bis-Tris buffer solution (pH 7.0), adsorbed on phenylcephalose CL4B column equilibrated with 10 mM bis-Tris buffer solution (pH 7.0), and then eluted with ammonium sulfate at a density gradient of 1 to 0M. The active fractions eluted by this operation were desalted with an ultrafiltration membrane, and lyophilized. In this procedure, 2.2 mg of lyophilized preparation was obtained.

The lyophilized preparation was white and confirmed to be a single entity upon electrophoresis on polyacrylamide gel.

Using this lyophilized preparation, optimum pH, pH stability, optimum temperature, thermal stability, influences of enzyme inhibitors and stability against surfactants were examined. FIGS. 1 to 5 show the results.

EXAMPLE 4

Washing test was conducted using the cellulase of the present invention as follows.

(a) Preparation of Soiled Cloth

About 200 ml of activated carbon was charged in a mortar and kneaded together with deionized water to obtain an aqueous suspension. In a pallette, cotton cloth was coated uniformly with this suspension, and dried in the air. Thereafter, the cloth was rubbed with a sponge 20 times to eliminate excess carbon. After being cut into pieces of a size of 5 cm×5 cm, the cloth pieces were subjected to washing tests.

(b) Washing Test

Washing was performed using Terg-O-Tometer under the conditions of rotation number of 120 rpm, at 30° C. for 10 minutes at a detergent concentration of 1330 ppm (using a JIS standard no-phosphor detergent).

Addition of the crude enzyme obtained in Example 2 in a concentration of 10 mg/liter resulted increase in whiteness by 5% and in laundry efficiency by 8% as compared with the detergent without addition of the enzyme.

EXAMPLE 5

As an example of utilization of the cellulase of the present invention in paper making processes, deinking test of waste newspaper was conducted as follows.

(a) Preparation of Pulp Slurry

Waste newspaper (9 g) was cut into pieces of a size of 5 cm×5 cm, introduced in 300 ml of deionized water, and left to stand at 45° C. for 30 minutes. The mixture was stirred in a mixer to prepare a pulp slurry.

The pulp slurry was adjusted to pH 9 with 0.1N NaOH, and subjected to deinking test.

(b) Deinking Test

To 20 ml of the adjusted pulp slurry was added 7 mg of the crude enzyme obtained in Example 2, and stirred at 45° C. for 1 hour.

The resulting mixture was filtrated with a 180 μm mesh wire gauze to recover the pulp. The pulp thus obtained was suspended in 200 ml of deionized water and filtrated with a 180 μm mesh wire gauze to wash the pulp, and then resuspended in 200 ml of deionized water.

The resulting pulp slurry (100 ml) was subjected to paper making by the use of a KIRIYAMA funnel with a diameter of 60 mm. After air drying, whiteness of paper was measured.

As compared with samples without addition of the enzyme, the samples of the invention in which 7 mg of the enzyme was added showed increase in whiteness by about 2%.

What is claimed is:

1. A composition comprising:
   (a) an isolated cellulase produced by Bacillus FERM BP-3431, or a mutant strain thereof, having the following properties:
   (1) an optimum pH range of 9.5 to 10.5 as measured using carboxymethylcellulose as a substrate;
   (2) a stable pH range of 6 to 11 as measured using carboxymethylcellulose as a substrate;
   (3) an optimum temperature of about 55° C. as measured using carboxymethylcellulose as a substrate;
   (4) influence of a surfactant being such that residual activity is 90% or more after treatment at 30° C. and pH of 9.0 for 2 hours in the presence of a sodium n-alkylbenzenesulfonate;
   (5) a molecular weight of 52,000±2,000 as measured by SDS-PAGE and
   (6) an isoelectric point of 4.2±0.2 as measured by PAGE; and
   (b) a paper pulp.

2. A method of treating a paper pulp slurry comprising:
   contacting said slurry with an amount of an isolated cellulase produced by Bacillus FERM BP-3431, or a mutant strain thereof, having the following characteristics:
   (1) an optimum pH range of 9.5 to 10.5 as measured using carboxymethylcellulose as a substrate;
   (2) a stable pH range of 6 to 11 as measured using carboxymethylcellulose as a substrate;
   (3) an optimum temperature of about 55° C. as measured using carboxymethylcellulose as a substrate;
   (4) influence of a surfactant being such that residual activity is 90% or more after treatment at 30° C. and pH of 9.0 for 2 hours in the presence of a sodium n-alkylbenzenesulfonate;
   (5) a molecular weight of 52,000±2,000 as measured by SDS-PAGE and
   (6) an isoelectric point of 4.2±0.2 as measured by PAGE.

3. The method of claim 2, wherein said cellulase is used in an amount of 0.1 to 2% per final weight of the slurry and wherein said cellulase has an activity of 100 u/g.

* * * * *

UNITED STATES PATENT AND TRADEMARK OFFICE
CERTIFICATE OF CORRECTION

PATENT NO. : 5,318,905
DATED : June 7, 1994
INVENTOR(S) : Saito, et al

It is certified that error appears in the above-indentified patent and that said Letters Patent is hereby corrected as shown below:

On the title page: Item [56]

change "2435 under "Foreign Patent Documents" 5/1990 Japan" to -- 2-435 1/1990 Japan --.

Column 1, line 2, kindly italicize "Bacillus Subtilis" and Column 2, line 3, italicize "Ruminococcus Flavefacienes" to be consistent with the style of italicizing species names.

Column 3, line 20, remove italics of "Pertitrichous flagella".

Column 7, line 23, change " $\mu$-glucoside" to -- $\beta$-glucoside --.

Column 8, line 2, change "when" to --When --.

Signed and Sealed this

Eighth Day of November, 1994

Attest:

BRUCE LEHMAN

*Attesting Officer*    *Commissioner of Patents and Trademarks*